(12) United States Patent
Hell et al.

(10) Patent No.: US 7,253,893 B2
(45) Date of Patent: Aug. 7, 2007

(54) METHOD AND APPARATUS FOR SPATIALLY LIMITED EXCITATION OF AN OPTICAL TRANSITION

(75) Inventors: Stefan Hell, Göttingen (DE); Marcus Dyba, Göttingen (DE)

(73) Assignee: Max-Planck-Gesellschaft zur Förderung der Wissenschaften e.V., Müchen (DE)

( * ) Notice: Subject to any disclaimer, the term of this patent is extended or adjusted under 35 U.S.C. 154(b) by 229 days.

(21) Appl. No.: 10/840,872

(22) Filed: May 7, 2004

(65) Prior Publication Data

US 2004/0207854 A1 Oct. 21, 2004

Related U.S. Application Data

(63) Continuation-in-part of application No. PCT/EP02/10456, filed on Sep. 18, 2002.

(30) Foreign Application Priority Data

Nov. 9, 2001 (DE) .................................. 101 54 699

(51) Int. Cl.
*G01J 3/42* (2006.01)
(52) U.S. Cl. ....................................................... 356/317
(58) Field of Classification Search ................ 356/317, 356/318, 417, 450; 250/459.1, 458.1, 461.1, 250/461.2
See application file for complete search history.

(56) References Cited

U.S. PATENT DOCUMENTS

| | | | | |
|---|---|---|---|---|
| 6,262,423 | B1* | 7/2001 | Hell et al. | 250/458.1 |
| 6,844,963 | B2* | 1/2005 | Iketaki et al. | 359/368 |
| 7,115,885 | B2* | 10/2006 | Hell | 250/459.1 |
| 2003/0132394 | A1* | 7/2003 | Wolleschensky et al. | 250/458.1 |

* cited by examiner

*Primary Examiner*—Gregory J. Toatley, Jr.
*Assistant Examiner*—Isiaka O. Akanbi
(74) *Attorney, Agent, or Firm*—Thomas, Kayden, Horstemeyer & Risley, LLP

(57) ABSTRACT

A method of exciting an optical transition in a narrowly limited area of a material comprising the steps of focusing an excitation light beam whose wavelength is tuned to the optical transition to be excited into a focal area extending beyond a focal point; splitting up a de-excitation light beam which is at least somehow influencing the optical transition into at least two partial beams; focusing the at least two partial beams of the de-excitation light beam out of different directions onto the focal point to form a spatially extending interference pattern in the focal area; adjusting a relative phase of the at least two partial beams of the de-excitation light beam so that the interference pattern has an intensity minimum at the focal point and a plurality of intensity maxima on different sides of the focal point; and aberrating the wave fronts of the at least two partial beams of the de-excitation light beam so that the intensity maxima of the interference pattern on different sides of the focal point are spatially expanded without eliminating the intensity minimum at the focal point.

27 Claims, 4 Drawing Sheets
(1 of 4 Drawing Sheet(s) Filed in Color)

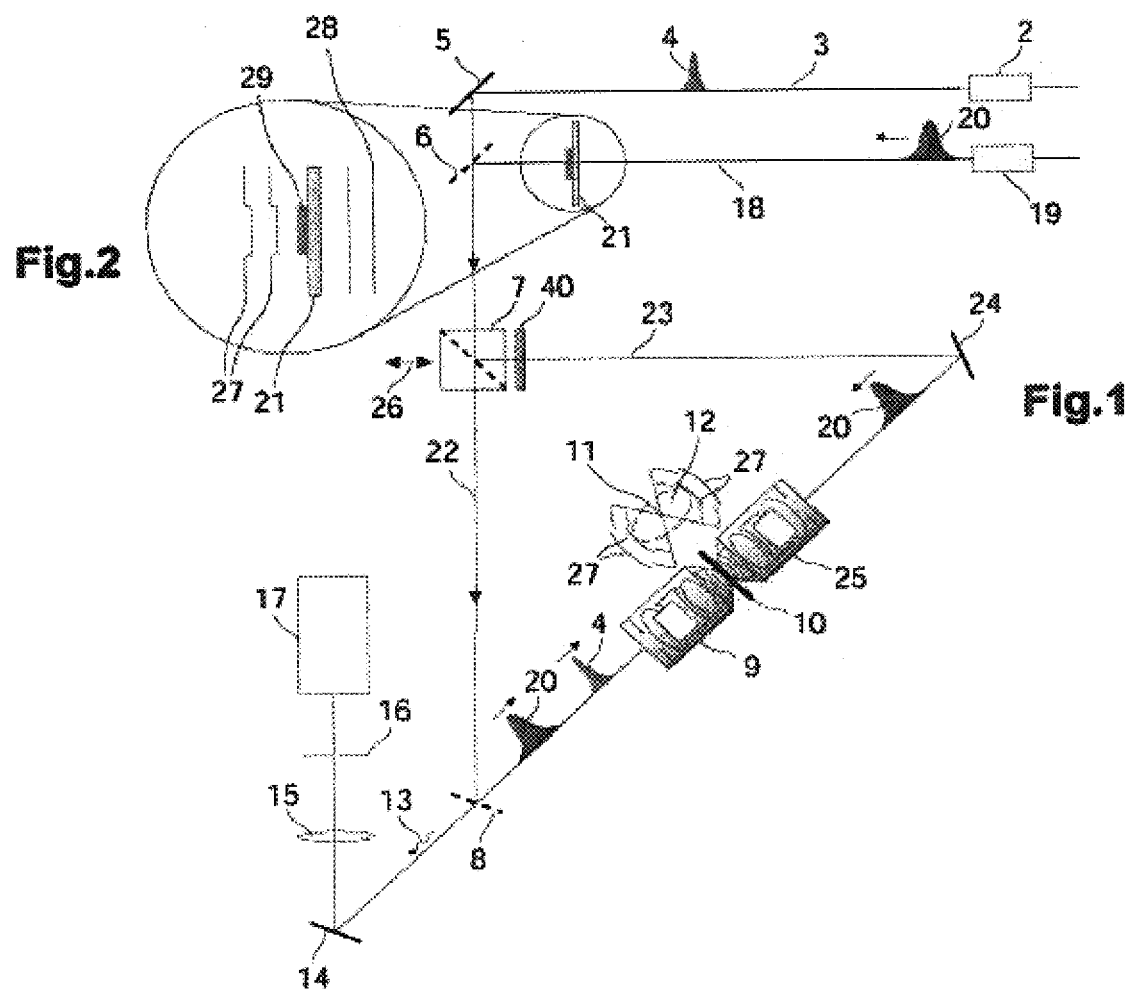

(a)
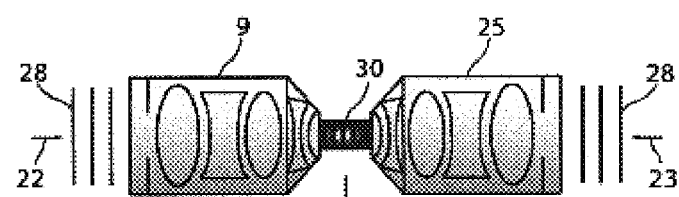
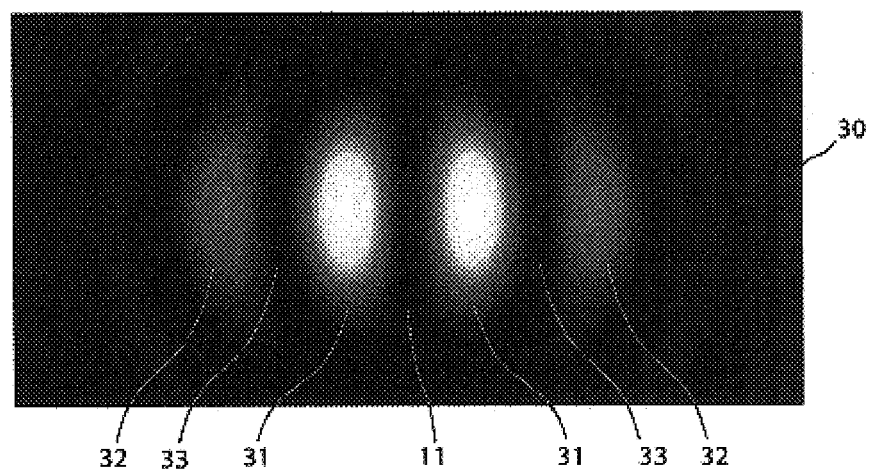
(b)
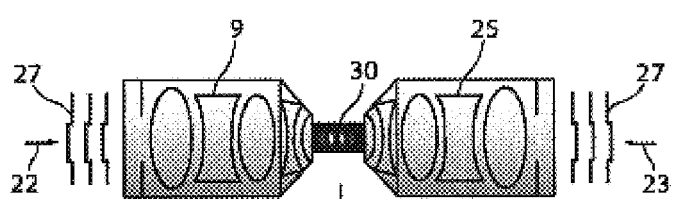
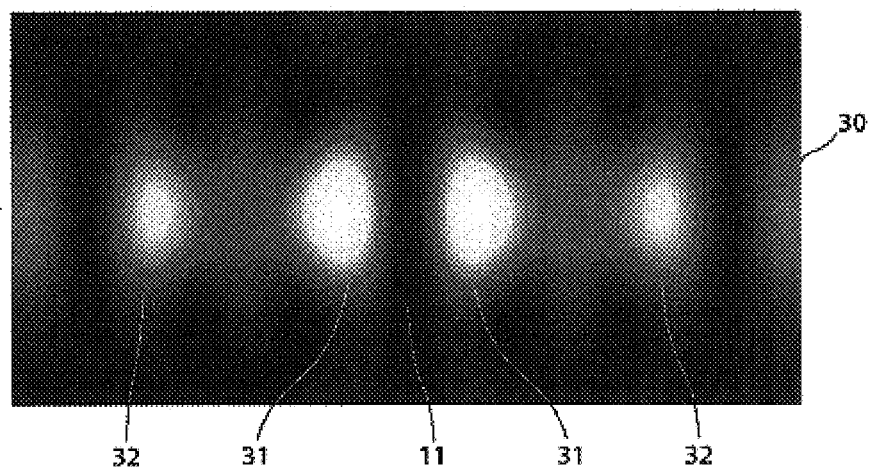
FIG. 3

METHOD AND APPARATUS FOR SPATIALLY LIMITED EXCITATION OF AN OPTICAL TRANSITION

CROSS REFERENCE TO RELATED APPLICATIONS

This application claims priority to co-pending German Patent Application No. 101 54 699.8 entitled "Verfahren und Vorrichtung zum räumlich eng begrenzten Anregen eines optischen Übergangs", filed Nov. 9, 2001, and is a Continuation in Part of International Patent Application PCT/EP02/10456 entitled "Method and Device for physically defined Excitation of an optical Transition", filed Sep. 18, 2002.

FIELD OF THE INVENTION

The invention generally relates to exciting an optical transition in a narrowly limited area of a material. More particularly, the invention relates to a method of exciting an optical transition in a narrowly limited area of a material, comprising the step of superimposing a focal spot of an excitation light beam extending beyond the focal point, the wavelength of the excitation light beam being tuned to the optical transition to be excited, with a spatial interference pattern of a de-excitation light beam that is somehow influencing the optical transition, the interference pattern having an intensity minimum at the focal point and a plurality of intensity maxima on different sides of the focal point.

Further, the invention relates to an apparatus for carrying out such a method comprising an excitation light source providing the excitation light beam, a first lens system for focusing the excitation light beam onto the focal point, a de-excitation light source providing the de-excitation light beam, a beam splitter splitting up the excitation light beam into the partial beams, one of the partial beams being focused onto the focus point by the first lens system, and at least a second tens system for focusing one of the other partial beams out of another direction onto the focus point to make the partial beams interfere.

BACKGROUND OF THE INVENTION

Already in 1873 Ernst Abbe found that beams of light coming from a light source are not focused by a lens into a zero-dimensional geometric focal point but, as a result of diffraction, only into a focal spot or focal volume extending around the geometric focal point. Normally diffraction leaves an elongated focal spot that is football-shaped. The minimum dimensions of this focal area are about Lambda/(2n), Lambda presenting the wavelength of the light, and n presenting the index of refraction. Along the optical axis the extension of the focal spot is at best only 4 times larger, namely 2×Lambda/(n). This barrier has various implications in many areas of technology. In fact, this applies to every application in which light is to be concentrated into a spatially limited area without contact. Examples encompass light microscopy, lithography, and the writing into optical data storage media.

In the field of fluorescence microscopy it is known from EP 0 801 759 B1 how to effectively reduce the area in which a sample is excited for fluorescence light emission to be specifically detected in a detector. According to that document the focal area of an excitation light beam is partially superimposed with the focal area of stimulation light beams which induce stimulated emission of the sample, by which the excited energy state of the sample out of which the spontaneous emission of fluorescence light takes place is de-excited again. Separation of the spontaneously emitted fluorescence light of interest from the light caused by the stimulated emission can be ensured by a disparity in wavelengths or by detecting the emitted fluorescence light at a different point in time. The spontaneously emitted fluorescence light, which is captured from the effectively reduced focal area of the excitation light beam, comes out of an area or volume which is smaller than the actual main focal area or volume of the excitation light beam.

A further starting point for reducing the effective focal area of a light beam is to produce an interference pattern in the focal area; to this end the excitation light beam is split up into partial beams, and the partial beams are superimposed with each other in a common focal area out of different directions so that the partial beams are preferably counter-propagating. The dimensions of the intensity maximum of this interference pattern now have a smaller extension of about Lambda/4n along the axis of counter-propagation. Located around the common geometric focal point, this main intensity maximum unfortunately is accompanied by at least two further secondary intensity maxima, situated in front of and behind the focal main maximum, but still within the common focal volume of the two partial beams.

From Stefan W. Hell "Increasing the Resolution of Far-Field Fluorescence Light Microscopy by Point-Spread-Function Engineering" in "Topics in Fluorescence Spectroscopy"; Volume 5: "Nonlinear and Two-Photon-Induced Fluorescence", edited by J. Lakowicz, Plenum Press, New York, 1997, page 417 following, a method is known to erase these secondary maxima. This method relies on superimposing the interference pattern of the partial beams of the excitation light beams with another interference pattern of partial beams of a stimulating light beam causing stimulated emission, the interference pattern of the stimulation light beam having a minimum at the focus point, i.e. featuring destructive interference at the geometric focal point, and the wavelength of the stimulation light beam being twice that of the wavelength of the excitation light beam. In this way, the maxima of the stimulation light beam located in front of and behind the focal point overlap with the secondary intensity maxima of the excitation light beam, so that only the main maximum of the excitation light beam around the focal point is effectively excited for spontaneous emission of fluorescence light which is detected. In this prior art, the limitation to those cases in which the stimulation light has twice the wavelength of the excitation light is a serious drawback. Besides, an apparatus for the realization of this method requires extremely high alignment efforts since both the excitation light beam and the stimulation light beam have to be split up into partial beams and to be focused out of opposite directions into the same focal area. Moreover, the phase differences of both pairs of partial beams have to be simultaneously adjusted and controlled with regard to the kind of interference at the common focal point of the partial beams. While the excitation partial beam pair has to be brought to constructive interference, the stimulating partial beam pair has to be brought to destructive interference at the same geometrical focal point. Thus, a corresponding apparatus has in fact up to now not been realized, although it should potentially enable to reduce the effective area of excitation of a sample by the excitation light beam far below the barrier of Lambda/2n.

The present invention is not limited to applications in fluorescence microscopes. Instead, it extends to all cases in which an optical transition may be excited by excitation light, and in which the optical transition can somehow be influenced or counteracted by de-excitation light. This includes the case that an energy state is de-excited with the de-excitation light by means of stimulated emission. However, it is also included that the de-excitation light depletes a ground state which is the only state out of which the optical transition can be excited by the excitation light. Further, the optical transition to be excited may initiate a photo-chemical process which is somehow inhibited or at least hindered by the de-excitation light. Thus, the term de-excitation light and de-excitation light beam, respectively, do not have another meaning in the context of this description than that the optical transition to be excited is somehow influenced or counteracted. For the invention it is important to reduce the effective area of the excitation of the optical transition by means of the de-excitation light beam. This does, for example, not mean that the superposition of the de-excitation light beam with the excitation light beam requires simultaneous or synchronized occurrence in the focal area as long as the desired effect of the de-excitation light beam is still given within a sequence in time.

SUMMARY OF THE INVENTION

In one aspect the present invention provides a method and an apparatus for exciting an optical transition of a material in a narrowly limited area which enable to reduce the area of the effective excitation of the optical transition by the excitation light beam to dimensions clearly smaller than Lambda/2n without large alignment efforts standing against their realization.

In a further aspect the present invention provides a method of exciting an optical transition in a narrowly limited area of a material comprising the steps of 1) focusing an excitation light beam, whose wavelength is tuned to the optical transition to be excited, into a focal area extending beyond a focal point; 2) splitting up a de-excitation light beam into at least two partial beams, which is at least somehow influencing the optical transition; 3) focusing the at least two partial beams of the de-excitation light beam out of different directions onto the focal point in order to form a spatially extending interference pattern in the focal area; 4) adjusting a relative phase of the at least two partial beams of the de-excitation light beam so that the interference pattern has an intensity minimum at the focal point and a plurality of intensity maxima on different sides of the focus point; and 5) aberrating the wave fronts of the at least two partial beams of the de-excitation light beam so that the intensity maxima of the interference pattern on different sides of the focal point are spatially expanded without degrading the intensity minimum at the focal point.

In the new method, the focal area or volume of the excitation light beam is superimposed with the interference pattern of the de-excitation partial light beams, the intensity maxima of the interference pattern formed on both sides of the focal point being blurred in such a way that the optical transition is effectively excited only in a spatially limited area around the focal point in which the interference pattern of the de-excitation light beam has an intensity minimum. Due to symmetry this intensity minimum is not affected by the aberration of the wave fronts of the partial de-excitation light beams. By contrast, in front of and behind the focal point, where there is no absolute symmetry between the wave fronts of the partial beams, the intensity maxima of the interference pattern become blurred so that the focal area of the excitation light beam can be covered with exception of the intensity minimum of the interference pattern at the focal point. Thus, the excitation of the optical transition is effectively confined to a small area around the focal point whose dimensions decrease far below the value of Lambda/2n. Spot sizes of excited material in the order of Lambda/10 and better may be achieved, which in turn leads to spatial resolutions of the same order.

In the new method it is preferred that the partial beams of the de-excitation light beam are focused onto the focal point from diametrical directions for forming the interference pattern, that is the partial beams counter-propagate. In case of the possible use of a system comprising more than two lenses for focusing the excitation light beam and the partial beams of the de-excitation light beam, an angle between the partial beams, preferably between 80 to 120° can, however, also be present.

In the new method, the excitation light beam is preferably not brought to interference with itself in the focal area because this is without an essential further advantage. At the same time it would considerably raise the alignment requirements in the application of the new method, because two interference patterns would then have to be adjusted with regard to each other.

A criterion for a sufficient expansion of the intensity maxima of the interference pattern of the de-excitation light beam to cover the focal area of the excitation light beam outside the focal point is that the first and the second order intensity maxima on both sides of the focal point overlap. This means that the zero intensity point between the first order and the second order intensity maxima on both sides of the focus point vanishes.

The wave fronts of the partial beams of the de-excitation light beam are preferably aberrated in the same way. This symmetry of the aberrated partial beams ensures that the interference intensity minimum at the focal point is kept at zero level, while the neighboring secondary minima are subject to blur induced by the abberation.

The wave fronts of the partial beams are aberrated in an identical and simple way in that the wave fronts of the de-excitation light beam are aberrated prior to the division into the partial beams. In this way, the aberrations of the wave fronts of both partial beams are identical so that there is no risk that the intensity minimum in the interference pattern of the partial beams at the focus point is affected.

In aberrating the wave fronts of the partial beams of the de-excitation light beam a central area of the wave fronts may be phase shifted with regard to its surrounding, for example.

If areas of the wave fronts are phase shifted with regard to each other in aberrating the wave fronts of the partial beams of the de-excitation light beam, it can also be preferred to effect a phase shift by more than the coherence length of the de-excitation light beam so that the de-excitation light from the different areas may no longer interfere in a destructive manner. Thus, the intensity minima of the interference pattern of the not aberrated partial beams are particularly effectively raised in their intensity.

In the new method, the partial beams are preferably focused onto the focus point with identical lens systems. The optics are preferably selected under the aspect of a high numerical aperture exceeding 1.0 as far as possible. A half aperture angle of more than 58° is preferred. As the excitation light beam is also focused onto the focal point through one of the two objective lenses, the focal area of the excitation light already has a spatial dimension that is, by known standards, as small as possible in the direction of the optical axis. The interference pattern of the two partial beams is also concentrated to this area.

In the new method, the excitation light beam and the de-excitation light beam may differ in their wavelengths and/or in their points in time of their incidence into the focal area and/or in the shapes of the laser pulses formed by them. Particularly, a single laser may both be used as a part of an excitation light source for the excitation light beam and as a part of a de-excitation light source for the de-excitation light beam.

The spatial resolution of the new method can principally be enhanced in that light intensities of a further de-excitation light beam are superimposed in the focal area with the excitation light beam. The further de-excitation light beam can be a de-excitation light beam which only differs from the first de-excitation light beam in the way of the aberration of the wave fronts of its partial beams so that the new method is also realized with the further de-excitation light beam. However, the further de-excitation light beam may also be a de-excitation light beam the wave fronts of the partial beams of which are not aberrated or which is not split into partial beams for forming an interference pattern so that it mainly makes use of principles known from the prior art. The employment of a further de-excitation light beam may particularly be considered for limiting the area of the effective excitation by the excitation light beam in a radial direction with regard to its axis, as a useful addition to the axial reduction of the area of effective excitation, which is the main subject of the new method. To this end, a simple further de-excitation light beam, i.e. a de-excitation light beam which is not brought to interference with itself, may be used whose core area is masked so that its remainder shows a doughnut-shaped intensity distribution around the focal point after focusing, and which in this way limits the effective excitation by the excitation light beam in all radial directions with regard to its axis.

Another addition to the new method is to accomplish the method steps in several focal areas which are arranged side by side and/or one behind the other at the same time. This can, for example, be accomplished by splitting up the excitation light beam and the de-excitation light beam in a plurality of partial beams running side by side, which are focused into a plurality of focal areas. Known means for such a beam splitting are pinhole and micro lens arrays.

In an actual embodiment of the new method the excitation light beam is used for exciting a sample for spontaneous emission of fluorescence light, and the de-excitation light beam is used for varying the excitation or for initiating stimulated emission of the sample, the spontaneously emitted fluorescence light being detected in a confocal way; it is to be noted, however, that the use of a confocal pinhole is optional. This procedure corresponds to fluorescence microscopy.

Besides the use of wavelength selective optical elements, a defined sequence in time may be used for separating the spontaneously emitted fluorescence light, in which the spontaneously emitted fluorescence light is only detected after the cessation of the de-excitation light beam which follows the excitation light beam or which is at least ending later than the excitation light beam. A synchronization of this kind, however, is known as such.

The excitation light beam can also be used for exciting a state which is a starting state of a photo-chemical process, and the de-excitation light beam can be used for inhibiting this photo-chemical process. In this way, for example, optical data carriers may be written. Also, for example, the photo-chemical process can be a switching of photo-chromic molecules performing a fluorescent and non-fluorescent state, where the de-excitation light beam switches the molecules into the non-fluorescent state.

In a further aspect the invention provides an apparatus for exciting an optical transition in a narrowly limited area of a material according to the new method which comprises an excitation light source providing an excitation light beam; a first lens system focusing the excitation light beam onto a focal point; a de-excitation light source providing a de-excitation light beam; a beam splitter splitting up the de-excitation light beam into at least two partial beams, one of the at least two partial beams being focused onto the focus point by the first lens system; at least a second lens system focusing one other of the at least two partial beams out of another direction onto the focal point to form an interference pattern spatially extending around the focal point; a phase adjusting element designed and arranged for adjusting the relative phase of the at least two partial beams; and an optical element which is designed and arranged for aberrating wave fronts of the at least two partial beams prior to them being focused onto the focal point.

Preferably, the first lens system and the second lens system are focusing the partial beams out of opposed directions, i.e. in a counter-propagating manner, onto the focus point.

Further, it is preferred that the possible beam paths are designed in such a way that no parts of the excitation light beam are getting into the focal area via the second lens system.

The optical element aberrating the wave fronts may be arranged in front of the beam splitter.

The optical element aberrating the wave fronts may comprise an optical element which varies the phase of the de-excitation light across the wave fronts. A possible embodiment of the aberrating optical element comprises, for example, a phase delay plate in its center introducing a phase step into the wave front. Other optical elements may also be used which effect other aberrations of the wave fronts, for example, a tilt or a curvature of the wave fronts.

Particularly preferred are optical elements aberrating the wave fronts which may be addressed by a computer to adjust the desired aberration. Optical elements of this kind are known and available in the form of active optical mirrors, like, for example, membrane mirrors with mechanical adjusting elements, and in the form of ferro-electrical optical elements, like, for example, liquid crystal elements.

Preferably, the two lens systems of the new apparatus are identical and have a half aperture angle of more than 58°.

For adjusting the intensity minimum of the interference pattern of the partial beams of the de-excitation light beam onto the focus point, a phase adjusting element is to be arranged in the beam path of one of the partial beams. This may also be a phase adjusting element in form of a beam splitter being movable with a piezo-actuator whose movements only have an effect on the path length of one of the partial beams.

In a preferred embodiment of the new apparatus only one active light source is provided which is directly used either as the excitation light source or the de-excitation light source. For providing the respective other light source, a passive non-linear optical element may be used. For example, the active light source is a pulsed laser, and the passive non-linear optical element is a frequency doubling crystal or an optical-parametric oscillator.

In the practical application of the new apparatus, it is important to adjust the partial beams of the de-excitation light beam to about the same intensity so that the interference pattern may indeed form an intensity zero-point at the focus point. An adjustable intensity decreasing means may be arranged in at least one of the two partial beams for tuning the intensities of the partial beams. The adjustable intensity decreasing means may comprise polarization optics or an optical cell filled with a solution of an absorbing material. Copper sulphate is suitable, for example.

A detector for capturing fluorescence light may be arranged in a plane which is conjugate with regard to the focus point, or likewise a confocal detector may be arranged for realizing a fluorescence microscope as an embodiment of the new apparatus.

The material may also consist of individual molecules that are dispersed on a surface or in solution, preferentially individual fluorescent molecules. These molecules may be marker molecules firmly attached to constituents of a biological cell, such as proteins and nucleic acids, viruses, or fractions thereof. The small effective focal area or volume of excitation may advantageously be used to detect individual or sparse molecules at low concentrations. In particular, the small volumes in which the molecules are effectively excited, that is provided by the method and apparatus claimed herein, can be used in conjunction with analysis by auto- or cross-correlation of the fluctuating fluorescence signal; that is, the method and apparatus of this invention can be combined with fluorescence correlation spectroscopy. The advantage of small volumes of effective excitation in fluorescence correlation spectroscopy is that dilute fluorescently marked compounds and fluorescent molecules can be observed and analyzed at higher concentrations.

Other features and advantages of the present invention will become apparent to one with skill in the art upon examination of the following drawings and the detailed description. It is intended that all such additional features and advantages be included herein within the scope of the present invention, as defined by the claims.

BRIEF DESCRIPTION OF THE DRAWINGS

The application file contains at least one drawing executed in color. Copies of this patent or patent application publication with color drawings will be provided by the Office upon request and payment of the necessary fee.

In the following the invention is further explained and described by means of an embodiment example which relates to the design of a fluorescence microscope which is, however, not intended as a corresponding limitation to the invention. The components in the following drawings are not necessarily to scale, emphasis instead being placed upon clearly illustrating the principles of the present invention. In the drawings, like reference numerals designate corresponding parts throughout the several views.

FIG. 1 shows the basic design of the new apparatus.

FIG. 2 shows the aberration of wave fronts in the new apparatus.

FIG. 3 shows the effect of the aberration of wave fronts on an interference pattern formed by the wave fronts coming out of diametric directions.

DETAILED DESCRIPTION

Figure 4:
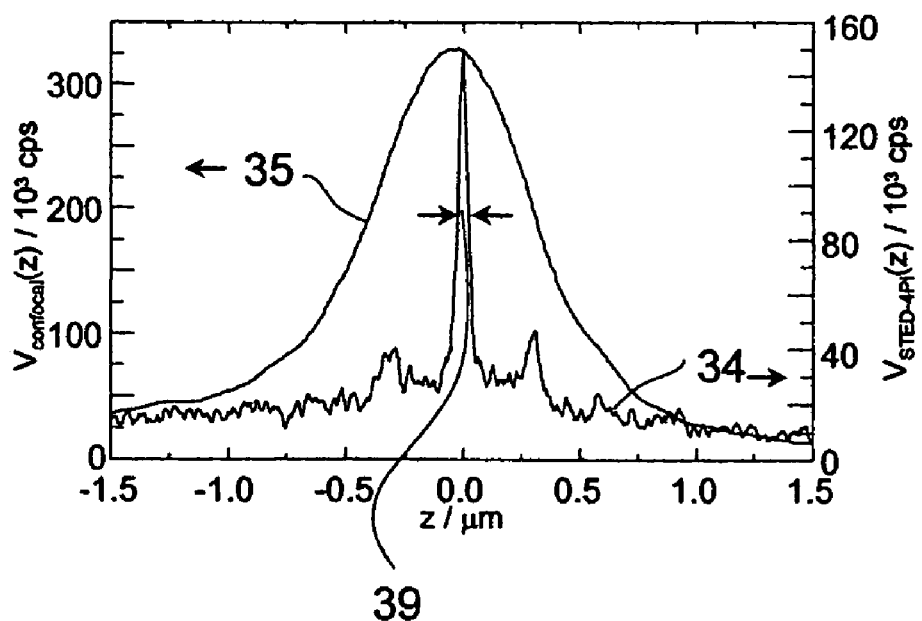
FIG. 4 is a first measurement result obtained with the new apparatus in comparison with a measurement result obtained with a confocal fluorescence microscope.

Referring now in greater detail to the drawings, the apparatus 1 schematically depicted in FIG. 1 comprises an excitation light source 2 providing an excitation light beam 3. The excitation light source 2 provides laser pulses 4 having a wavelength of 554 nm and a pulse duration of 250 fs. The excitation light beam 3 is directed into a first lens system 9 via a mirror 5, through a first dichroic mirror 6 and a beam splitter 7 as well as via a second dichroic mirror 8, and is then focused by the lens system 9 in the area of a sample 10 onto a focal point 11 which is depicted here in an enlarged detail picture besides the sample 10. A partial beam split off from the excitation light beam 3 in the beam splitter 7 is blocked by a wavelength selective element 40 which has no transmission for light having the wavelength of the excitation light beam 3. Because of the diffraction barrier, the excitation light beam 3 is actually not only focused into the zero-dimensional focal point 11 but into a focal area or volume 12 which has a certain spatial extension particularly in the direction of the optical axis of the lens system 9. In the whole focal area 12 an excitation of the sample 10 into an excited energy state takes place out of which the sample 10 spontaneously emits fluorescence light 13 which propagates back through the lens system 9 and the dichroic mirror 8, whose transmission wavelength is tuned to the wavelength of the fluorescence light 13, and via a mirror 14 as well as through a lens 15 and a pinhole 16 into a detector 17. The pinhole 16 is in a confocal arrangement with regard to the focal point 11 to enhance the spatial resolution in the registration of the fluorescence light with the detector 17. Here, however, the essential enhancement with regard to the spatial resolution in detecting the fluorescence light is achieved by means of a de-excitation light beam 18 which comes from a de-excitation light source 19. The de-excitation light source 19 provides laser pulses 20 of 13 ps duration and with a wavelength in the area of 750 nm. Whereas the wavelength of the excitation light beam 3 is tuned for an excitation of an energy state of the sample 10 out of which the sample spontaneously emits fluorescence light, the wavelength of the de-excitation light beam 18 is selected in such a way that a stimulated emission of the sample 10 is initiated which de-excites the excited energy state. By superimposing the de-excitation light beam 18 with the excitation light beam 3 in the focal area 12 in a certain way, the area out of which the detector 17 receives fluorescence light 13 may be spatially limited to a smaller area around the focus point 11. The detector 17 or an optical element connected in series (not depicted here) may separate the stimulated emission of the sample 10 by means of a wavelength differing from the fluorescence light 13, or the separation may be done by timing in that at first a laser pulse 4 of the excitation light beam 3 and then a laser pulse 20 of the de-excitation light beam 18 are directed onto the sample 10, and that only later, after the laser pulse 20 and the stimulated emission of the sample 10 initiated by it are decayed, the detector 17 is activated for receiving the spontaneously emitted fluorescence light from the sample 10.

To de-excite the sample with the de-excitation light beam 18 everywhere outside the focal point 11 but to leave it unaffected at the focal point 11, the de-excitation light beam 18 is first sent through an optical element 21 aberrating its wave fronts. After that, the de-excitation light beam 18 is joined with the excitation light beam 3 by means of the dichroitic mirror 6 which is reflecting at the wavelength of the de-excitation light beam 18. In the beam splitter 7 the de-excitation light beam 18 is split up into two partial beams 22 and 23. The partial beam 22 is guided in the same way as the excitation light beam. The partial beam 23 passes through the wavelength selective element 40 which is transmissive at the wavelength of the de-excitation light beam 18 and via a mirror 24 to the second lens system 25 which is identical to the lens system 9. By the lens system 25 the partial beam 23 is focused onto the focus point 11. In this way the de-excitation light beam is superimposed with itself in the focus area 12 in form of its partial beams 22 and 23. An interference pattern occurs. The phase position of the interference pattern with regard to the focus point 11 is adjusted in such a way that an intensity minimum is formed at the focus point 11. This is done by moving the beam splitter 7 in the direction of a double arrow 26 by means of a piezo-actuator, for example. The movement of the beam splitter 26 only has an effect on the beam path of partial beam 23 and thus on the relative phase position of the partial beams 22 and 23 with regard to each other. The interference pattern of the partial beams 22 and 23 is distorted by their aberrated wave fronts 27 in a sense that the intensity maxima on both sides of the focus point 11 are smeared out so that the higher order intensity minima of the interference pattern are raised in their intensity. This will be explained more detailed with reference to FIG. 3 below.

FIG. 2 shows the effect of the optical element 21 onto the incoming flat wave fronts 28 of the de-excitation light beam 18. By means of a phase plate 29 in the center of the optical element 21 the phase of the wave fronts 28 is locally delayed, resulting into step-shaped aberrated wave fronts 27 which are indicated next to the focus point 11 in FIG. 2. Other aberrations are usable and suitable in the same way. It is important that the flat wave fronts are sufficiently deformed for an overlap of the intensity maxima in the interference pattern of the partial beams 22 and 23 on both sides of the focus point 11.

In its upper part (a), FIG. 3 shows the formation of an interference pattern 30 by flat wave fronts 28 getting out of the lens systems 9 and 25 according to FIG. 1 into the focus area 12. Here, it can be seen that on both sides of the focus points 11 in the middle of the interference pattern 30 two intensity maxima 31 and 32 of first and second order are formed. These intensity maxima are clearly separated by intensity minima 33 being in between. In contrast, FIG. 3(b), below sketches the effect which is achieved by the aberrated wave fronts 27 with regard to the interference pattern 30. The intensity maxima 31 and 32 of first and second order are slightly expanded away from the focus point 11, and, especially, they are expanded to such an extent that they overlap in the area of the intensity minimum 33 according to FIG. 3(a) which was previously existing there, and that the intensity of the de-excitation light is raised there. For symmetry reasons, however, the intensity minimum at the focal point 11 remains. Thus, by means of the interference pattern 30 according to FIG. 3(b), the excitation of the sample 10 can be set back within the whole focus area 12 according to FIG. 1 except in the immediate proximity of the focal point 11. Accordingly, fluorescence light may be detected whose origin is concentrated to a very limited area around the focal point 11.

As an example, FIG. 4 shows the signal of the detector 17 over the sample depth z [µm] upon using water immersion lens systems 9 and 25 having a numerical aperture of 1.2 in the case of a thin fluorescence layer in the sample. The detector signal 34 of the apparatus 1 according to FIG. 1 is here compared with the detector signal 35 of a corresponding confocal fluorescence microscope. The clearly smaller full width at half maximum 39 of the signal 34 around the position of the fluorescence layer is evident. The full width at half maximum is only 46±5 nm, here. This is clearly smaller than a $10^{th}$ part of the wavelength of the excitation light beam. The full width at half maximum of the signal 35 of the confocal fluorescence microscope is larger by an order of magnitude.

Figure 5:
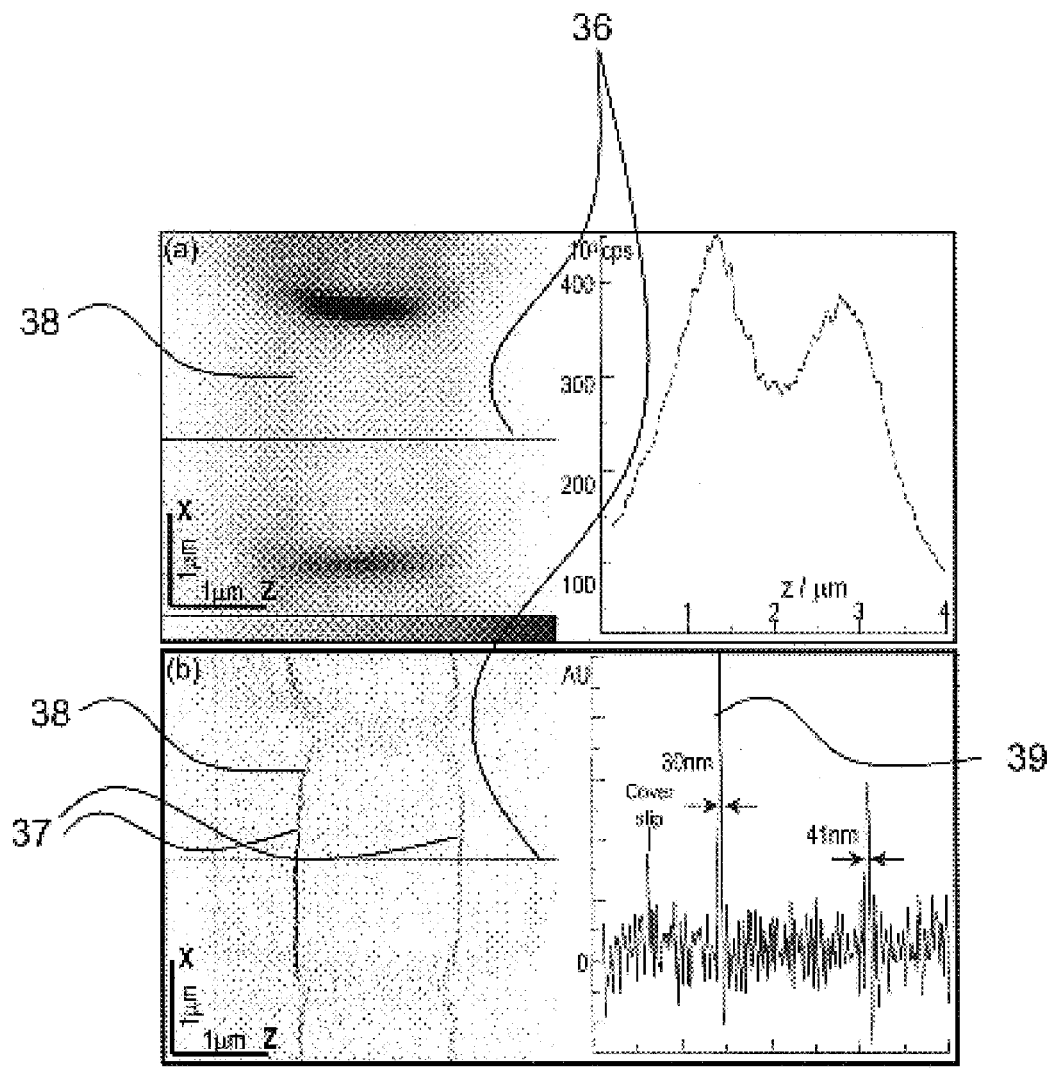
FIG. 5 is a second measurement result obtained with the new apparatus again in comparison with a measurement result obtained with a a confocal fluorescence microscope.

FIG. 5 shows images of a bacterium whose membranes are marked with a fluorescence dye. FIG. 5(a) shows a two-dimensional optical section image, i.e. an image containing the optical axis as a coordinate, of the bacterium on the left hand side, and the slope of the signal along a line 36 depicted in the image of the bacterium on the right hand side, which are both recorded with a confocal fluorescence microscope. In comparison, FIG. 5(b) shows corresponding recordings obtained with the apparatus 1 according to FIG. 1. Here, the resolution of the membranes 37 of the bacterium 38 is much better and sharper. By means of linear mathematical filtering of the signal according to FIG. 5(b) residual fluorescence in the neighboring areas to the membranes in the image and an even higher enhancement of the resolution can be achieved.

The focal point of the excitation beam need not perfectly coincide with the common focal point of the partial de-excitation beams. It is sufficient that the main focal volume of the excitation beam largely overlaps with the central minimum of the interference pattern of the partial de-excitation beams.

Many variations and modifications may be made to the preferred embodiments of the invention without departing substantially from the spirit and principles of the invention. All such modifications and variations are intended to be included herein within the scope of the present invention, as defined by the following claims.

LIST OF REFERENCE NUMERALS

1 Device
2 Excitation light source
3 Excitation light beam
4 Laser pulse
5 Mirror
6 Mirror
7 Beam splitter
8 Mirror
9 Lens system
10 Sample
11 Focal point
12 Focal area
13 Fluorescence light
14 Mirror
15 Lens
16 Pinhole
17 Detector
18 De-excitation light beam
19 De-excitation light source
20 Laser pulse
21 Optical element
22 Partial beam
23 Partial beam
24 Mirror
25 Lens system
26 Double arrow
27 Aberrated wave front
28 Wave front
29 Phase plate
30 Interference pattern 31 Intensity maximum
32 Intensity maximum
33 Intensity minimum
34 Detector signal
35 Detector signal
36 Line
37 Membrane
38 Bacterium
39 Full width at half-maximum
40 Wavelength selective element

We claim:

1. A method of exciting an optical transition in a narrowly limited area of a material, the methods comprising the steps:
   focusing an excitation light beam whose wavelength is tuned to the optical transition to be excited in a focal area extending beyond a focal point;
   splitting up a de-excitation light beam which is at least somehow influencing the optical transition into at least two partial beams;
   focusing the at least two partial beams of the de-excitation light beam from different directions onto the focal point to form a spatially extending interference pattern in the focal area;
   adjusting a relative phase of the at least two partial beams of the de-excitation light beam so that the interference pattern has an intensity minimum at the focal point and a plurality of intensity maxima on different sides of the focal point; and
   aberrating the wave fronts of the at least two partial beams of the de-excitation light beam so that the intensity maxima of the interference pattern on different sides of the focal point are spatially expanded without eliminating the intensity minimum at the focal point.

2. The method of claim 1, wherein the at least two partial beams are focused onto the focal point out of diametrical directions.

3. The method of claim 1, wherein the excitation light beam is focused into the focal area out of one direction only.

4. The method of claim 1, wherein the intensity maxima of the interference pattern are spatially expanded to such an extent that a zero intensity point between first and second order intensity maxima on both sides of the focal point vanishes.

5. The method of claim 1, wherein the wave fronts of the partial beams of the de-excitation light beam are aberrated in the same way.

6. The method of claim 5, wherein the step of aberrating the wave fronts of the partial beams includes aberrating the wave fronts of the de-excitation light beam prior to splitting it up into the partial beams.

7. The method of claim 6, wherein aberrating the wave fronts of the de-excitation light beam includes phase shifting a central area of the wave fronts with regard to its surrounding areas.

8. The method of claim 7, wherein phase shifting a central area of the wave fronts with regard to its surrounding areas includes phase shifting by more than the coherence length of the de-excitation light beam.

9. The method of claim 1, wherein the partial beams are focused onto the focus point with identical lens systems having a half aperture angle of more than 58°.

10. The method of claim 1, wherein the excitation light beam and the de-excitation light beam differ in their wavelengths.

11. The method of claim 1, wherein the excitation light beam and the de-excitation light beam differ in their points in time of their incidence into the focus area.

12. The method of claim 1, wherein the excitation light beam and the de-excitation light beam differ in shapes of the laser pulses forming them.

13. The method of claim 1, wherein the excitation light beam is used for exciting the material in a sample for spontaneous emission of fluorescence light, and the de-excitation light beam is used for inhibiting the excitation of the material, the spontaneously emitted fluorescence light being detected in a confocal way.

14. The method of claim 1, wherein the excitation light beam is used for exciting the sample material for spontaneous emission of fluorescence light, and the de-excitation light beam is used for initiating stimulated emission of the material, the spontaneously emitted fluorescence light being detected in a confocal way.

15. The method of claim 1, wherein the excitation light beam is used for exciting a state of the material which is a starting state of a photo-chemical process, and that the de-excitation light beam is used for inhibiting this photo-chemical process.

16. The method of claim 1, wherein the signal of at least one fluorescent molecular species is detected to the end of recording the auto-correlation function of the fluctuating fluorescence signal.

17. The method of claim 1, wherein the signals of at least two fluorescent molecular species are detected to the end of recording the cross-correlation function of the fluctuating fluorescence signal of different species.

18. An apparatus for exciting an optical transition in a narrowly limited area of a material, the apparatus comprising:
   an excitation light source providing an excitation light beam;
   a first lens system focusing the excitation light beam onto a focal point from one direction;
   a de-excitation light source providing a de-excitation light beam;
   a beam splitter splitting up the de-excitation light beam into at least two partial beams, one of the at least two partial beams being focused onto the focal point by the first lens system;
   at least a second lens system focusing one other of the at least two partial beams from another direction onto the focal point to form an interference pattern spatially extending around the focal point;
   a phase adjusting element designed and arranged for adjusting the relative phase of the at least two partial beams; and
   an optical element which is designed and arranged for aberrating wave fronts of both of the at least two partial beams prior to them being focused onto the focus point.

19. The apparatus of claim 18, wherein the first lens system and the second lens system are directed onto the focus point out of diametrically opposed directions.

20. The apparatus of claim 18 wherein no parts of the excitation light beam are getting into the focus area via the second lens system.

21. The apparatus of claim 18, wherein the optical element aberrating the wave fronts is arranged in front of the beam splitter in a beam path of the not yet split-up de-excitation light beam.

22. The apparatus of claim 19, wherein the optical element aberrating the wave fronts comprises an optical element which varies the phase of the de-excitation light across the wave fronts.

23. The apparatus of claim 18, wherein the two lens systems are identical.

24. The apparatus of claim 21, wherein the two lens systems each have a half aperture angle of more than 58°.

25. The apparatus of claim 18, wherein the phase adjusting element is arranged in a beam path of one of the partial beams.

26. The apparatus of claim 18, and further comprising a detector for capturing fluorescence light which is arranged in a confocal arrangement with regard to the focal point.

27. An apparatus for exciting an optical transition in a narrowly limited area of a material, the apparatus comprising:
- an excitation light source providing an excitation light beam whose wavelength is tuned to the optical transition to be excited;
- a first lens system focusing the excitation light beam into a focus area extending beyond a focal point from a first direction;
- a de-excitation light source providing a de-excitation light beam which is at least somehow influencing the optical transition;
- a beam splitter splitting up the de-excitation light beam into at least two partial beams, one of the at least two partial beams being focused onto the focal point by the first lens system;
- at least a second lens system focusing one other of the at least two partial beams from another direction onto the focal point to form an interference pattern spatially extending around the focal point;
- a phase adjusting element designed and arranged for adjusting the relative phase of the at least two partial beams of the de-excitation light beam so that the interference pattern has an intensity minimum at the focal point and a plurality of intensity maxima on different sides of the focal point; and
- an optical element which is designed and arranged for aberrating wave fronts of both of the at least two partial beams prior to them being focused onto the focal point so that the intensity maxima of the interference pattern on either sides of the focal point are spatially expanded without eliminating the intensity minimum at the focal point.

* * * * *